United States Patent [19]

Hossain et al.

[11] Patent Number: 5,125,891
[45] Date of Patent: Jun. 30, 1992

[54] DISPOSABLE VACUUM/PERISTALTIC PUMP CASSETTE SYSTEM

[75] Inventors: K. Mosaddeq Hossain, Hillsborough, N.J.; Jude V. Paganelli, New Britain, Pa.; Bernd R. Fischer, E. Norristown, Pa.; Robert M. Bross, Ivyland, Pa.; Kenneth P. Cook, Blue Bell, Pa.

[73] Assignee: Site Microsurgical Systems, Inc., Horsham, Pa.

[21] Appl. No.: 253,801

[22] Filed: Oct. 5, 1988

Related U.S. Application Data

[63] Continuation-in-part of Ser. No. 43,120, Apr. 27, 1987, Pat. No. 4,798,580.

[51] Int. Cl.⁵ .............................................. A61M 1/00
[52] U.S. Cl. .................................. 604/34; 604/153; 604/250; 417/477
[58] Field of Search ........................... 604/22, 30–35, 604/118–120, 67, 153, 250, 317; 128/DIG. 12, DIG. 13; 417/474–477, 360

[56] References Cited

U.S. PATENT DOCUMENTS

| | | | |
|---|---|---|---|
| 3,723,030 | 3/1973 | Gelfand | 417/475 |
| 3,841,799 | 10/1974 | Spinosa et al. | 417/477 |
| 4,168,707 | 9/1979 | Douvas et al. | 128/276 |
| 4,187,057 | 2/1980 | Xanthopoulos | 417/63 |
| 4,256,437 | 3/1981 | Brown | 417/45 |
| 4,256,442 | 3/1981 | Lamadrid et al. | 417/477 |
| 4,424,011 | 1/1984 | O'Brien et al. | 417/477 |
| 4,445,826 | 5/1984 | Tarr | 417/476 |
| 4,464,172 | 8/1984 | Lichtenstein | 604/65 |
| 4,479,760 | 10/1984 | Bilstad et al. | 417/395 |
| 4,482,347 | 11/1984 | Borsanyi | 604/153 |
| 4,493,695 | 1/1985 | Cook | 604/22 |
| 4,515,589 | 5/1985 | Austin et al. | 604/122 |
| 4,526,515 | 7/1985 | DeVries | 417/63 |
| 4,537,561 | 8/1985 | Xanthopoulos | 417/63 |
| 4,599,055 | 7/1986 | Dykstra | 417/477 |
| 4,627,833 | 12/1986 | Cook | 604/34 |
| 4,650,469 | 3/1987 | Berg et al. | 604/131 |
| 4,685,902 | 8/1987 | Edwards et al. | 604/153 |
| 4,713,051 | 12/1987 | Steppe et al. | 604/30 |
| 4,714,464 | 12/1987 | Newton | 604/118 |
| 4,735,558 | 4/1988 | Kienholz et al. | 417/477 |
| 4,735,558 | 4/1988 | Lienholz et al. | 417/477 |
| 4,758,238 | 7/1988 | Sundbloom et al. | 604/319 |
| 4,798,580 | 1/1989 | DeMeo et al. | 604/30 |
| 4,820,265 | 4/1989 | DeSatnick et al. | 604/30 |
| 4,838,865 | 6/1989 | Flank et al. | 604/118 |
| 4,900,302 | 2/1990 | Newton | 604/30 |
| 4,933,843 | 6/1990 | Scheller et al. | 304/413.01 |

Primary Examiner—John D. Yasko
Assistant Examiner—Adam J. Cermak
Attorney, Agent, or Firm—Paul A. Coletti

[57] ABSTRACT

A microsurgical irrigation/aspiration system is provided, including a controller having a pump roller head, actuators for occluding fluid lines, a suction sensor, and means for mounting a pump cassette. The system cassette is suitable for mounting on the controller and has an opening with a pump segment passing along an arcuate wall of the opening. When the cassette is mounted on the console, the roller head is engaged in the cassette opening and compresses the pump segment against the arcuate wall. An infusion line passes through the cassette and is occludable by one of the actuators, and a vent line connected to the pump segment is occludable by a second actuator. A suction sensing port on the cassette couples with the suction sensor in the controller. In an alternate embodiment, a cassette is disclosed within which both vacuum and peristaltic pumping is possible. Latching may be accomplished by a plunger attached to the sensory port of the cassette.

31 Claims, 11 Drawing Sheets

DISPOSABLE VACUUM/PERISTALTIC PUMP CASSETTE SYSTEM

This application is a continuation-in-part of Ser. No. 043,120 entitled "Disposable Peristaltic Pump Cassette System", filed Apr. 27, 1987, now U.S. Pat. No. 4,798,580, issued Jan. 17, 1989.

This invention relates to peristaltic pumps and, in particular, to peristaltic pump systems with disposable cassettes adaptable for use in ophthalmic microsurgery. In addition, the present invention particularly relates to vacuum pump systems incorporated with the peristaltic pump system using disposable cassettes adaptable for use in ophthalmic microsurgery.

In ophthalmic microsurgery, commonly employed surgical instruments such as electro-mechanical or pneumatically driven cutters and phacoemulsification instruments require a source of liquid to infuse a surgical site, and a source of negative pressure to evacuate the infusion liquid and debris from the site. Systems which perform these liquid flow functions for microsurgical instruments are commercially available, and are known as infusion/aspiration systems. One such system which has gained widespread acceptance is the SITE TXR ® system, the fundamental principles of which are described in U.S. Pat. No. 4,493,695. That patent describes a cassette assembly which mounts on a modular control console. The control console interfaces with the cassette to provide a source of vacuum for a suction line connected between the cassette and the surgical instrument, and control means for controlling the application of suction and infusion fluid for the instrument. Connected to the cassette and in fluid communication with the suction line is a collection bottle which collects the aspirated liquid and debris from the surgical site. For each surgical procedure a new cassette and collection bottle are mounted on the console and the cassette and bottle are disposed of after the procedure, thereby insuring that a completely sterile fluid system is used for each procedure.

The console of the patented system includes a diaphragm vacuum pump which provides the source of suction for the cassette. Another mechanism which is capable of supplying a negative fluid pressure for medical apparatus is the peristaltic pump, which is desirable for its ability to provide liquid suction. A peristaltic pump generally includes a motor driven head containing a number of rollers. A section of collapsible tubing is securely mounted around the roller head by a clamping mechanism. As the roller head turns, individual rollers sequentially compress the tubing and squeeze liquid through it in the direction of rotation of the roller head.

When a peristaltic pump is used in an infusion/aspiration system, the previously described need for sterility of the fluid system is still present. It is desirable for a disposable system for the peristaltic pump to provide all of the fluid control required in an infusion/aspiration system. The disposable system should be economical to produce so it can be disposed of after use without incurring a large expense. The disposable system should also be compact so as to require a minimal storage area in a hospital or other medical facility.

In accordance with the principles of the present invention a peristaltic pumping system for infusion/aspiration procedures is provided which includes a disposable pump cassette. The system includes a console with a roller head, means for mounting the cassette over the roller head, and interrupter bars for occluding the tubing and flow of infusion fluid in the cassette. An infusion fluid line passes through the cassette, and is aligned with an interrupter bar in the console. The interrupter bar is selectably controlled to control the flow of infusion liquid to the surgical site. A suction line is connected to the cassette and is curved around an arcuate opening in the cassette which is located around the roller head. Rotation of the roller head will thereby draw liquid from the surgical site through the suction line.

In a preferred embodiment of the present invention, a pressure sensing port is connected to the suction line of the cassette. The pressure sensing port connects to a pressure sensor within the console, which monitors the suction pressure and supplies feedback to control the pump. A constructed embodiment of the cassette of the present invention is very compact, measuring about 3.5 inches by 4 inches by one-half inch thick, and is economical to manufacture and assemble.

In accordance with the principles of the present invention, there is also disclosed a dual peristaltic pumping/diaphragm vacuum system for infusing/aspiration procedures which includes a disposable pump cassette. The system includes a console with either a peristaltic head or a vacuum diaphragm head, wherein either can be positioned in place in order to accept the disposable pump cassette. There are means for mounting the cassette over the pumping system, and interrupter means for occluding the line in the cassette. An infusion fluid line passes through the cassette, and is aligned with the interrupter means in the console. The interrupter means can be selectively controlled to control the flow of infusion liquid to the surgical site.

The suction line is connected to the cassette and is curved around an arcuate opening in the cassette which is located around the pumping system. Where peristaltic pumping is used, the suction line is curved around the arcuate opening in order to accept the roller heads of the peristaltic pump. Where vacuum suction is used, the suction line opens into the vacuum diaphragm system. In either event, the pump systems will draw liquid from the surgical site through the suction line.

In this preferred embodiment of the present invention, a pressure sensing port is also connected to the suction line of the cassette. The port connects to a pressure sensor within the console, which monitors the suction pressure. A constructed embodiment of this cassette of the present invention is also very compact, measuring about 4 inches by 4 inches by 1 inch thick, and is also economical to manufacture and assemble.

Figure 1:
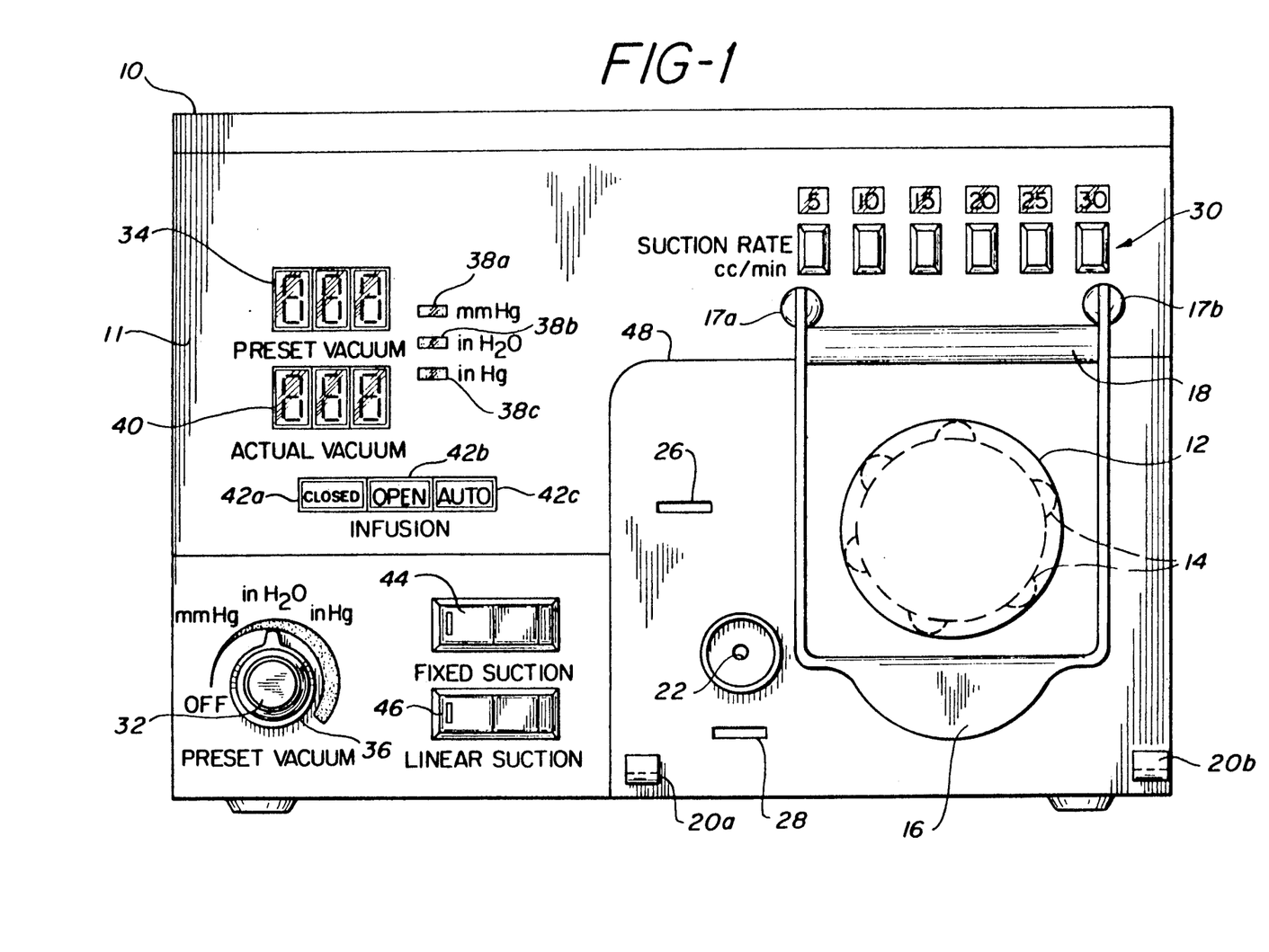
FIG. 1 illustrates a peristaltic pump module constructed in accordance with the principles of the present invention.

Referring to FIG. 1, a peristaltic pump module 10 constructed in accordance with the principles of the present invention is shown. A constructed embodiment of this module has been built as a modular add-on to the SITE TXR ® system. This mainframe system includes a chassis which can accommodate a number of modules that perform different functions for the ophthalmic surgeon, including the control of surgical cutting instruments and infusion and aspiration. The module shown in FIG. 1 is representative of one of these modules which provides infusion and peristaltic pump aspiration.

On the front panel 11 of the module are a number of controls and displays. A concentric switch includes a center knob 32 which turns the module on and is adjustable to set the maximum suction level to be applied by the peristaltic pump. As the knob 32 is adjusted the numbers displayed by the preset vacuum display 34 will vary to indicate the setting of the maximum vacuum. The outer knob 36 is adjustable to one of three settings: mm Hg, in. H₂O, and in. Hg. The setting of knob 36 illuminates one of three corresponding lights 38a, 38b, or 38c, which inform the user as to the units in which the vacuum measurements are being displayed by displays 34 and 40. The display 40 constantly displays the vacuum level at the inlet (suction) line to the peristaltic pump. A pressure sensor accesses the suction line through a port 22.

Three pushbuttons 42a, 42b, and 42c provide control of the liquid infusion line. When the "auto" pushbutton 42c is depressed, the infusion line is opened automatically whenever a control pedal (not shown) is depressed to start the pump, and is automatically occluded by the extension of a solenoid actuated interrupter bar through opening 26 when the control pedal is released. The other two pushbuttons provide manual control of the infusion line. When "closed" pushbutton 42a is depressed, the interrupter bar extends to occlude the infusion line, and when "open" pushbutton 42b is depressed the interrupter bar retracts to open the line. The control functions of pushbuttons 42a and 42b operate independently of the control pedal.

The pump speed, and hence the rate at which the vacuum level is developed by the pump, is set by depressing one of pushbuttons 30. Each pushbutton controls the suction rate, as measured in cubic centimeters of flow per minute through an unblocked suction line.

Two types of suction control are available. When the "fixed suction" switch 44 is set, the pump will immediately begin pumping at the preset suction rate when the control pedal is depressed. When the "linear suction" switch 46 is set, the operator can accelerate the suction rate up to the preset rate by controllably depressing the control pedal.

The pump mechanism includes a brushless DC motor and gearbox located within the module which rotates a pump head 12. Evenly spaced around the pump head are six rollers 14. The pump head is turned in a clockwise direction by the motor so that the rollers will sequentially and smoothly squeeze the pump tubing as they pass along the upper quadrant of the pump head location. Included in the pump mechanism is a more conventional vacuum pump not shown which can alternately be used to replace the peristaltic pump system. The vacuum pump is akin to that described in the previously referenced U.S. Pat. No. 4,493,695.

The pump cassette, to be described below, is affixed in an area outlined by 48. The cassette is supported at the bottom by the placement of tabs at the bottom corners of the cassette in two retaining brackets 20a and 20b. The cassette is held in place by a cam bar 18 at the top of the cassette. The cam bar is secured between the sides of a latch 16, which is pivotally connected to latch supports 17a and 17b above the area 48. When the cassette is placed in position with its tabs located in the brackets 20a and 20b, the latch may be swung down so that the cam bar engages the upper edge of the cassette. The latch is then pressed firmly against the front surface of the cassette, causing the cam bar to roll to the center of the cassette top which presses the suction tubing of the cassette against the pump head. The cam bar distributes pressure equally across the top of the mounted cassette.

A second solenoid actuated interrupter bar controllably extends through opening 28 in the front panel to selectively open or occlude a vent line to the suction line of the cassette.

Figure 2:
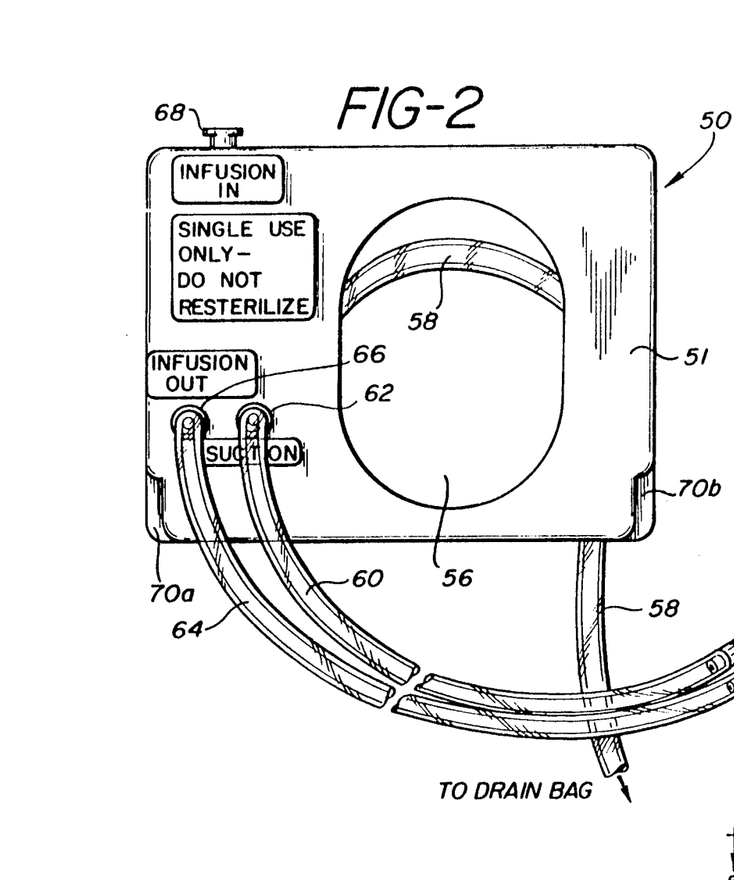
FIG. 2 is a front plan view of a peristaltic pump cassette suitable for use with the module of FIG. 1.
Figure 3:
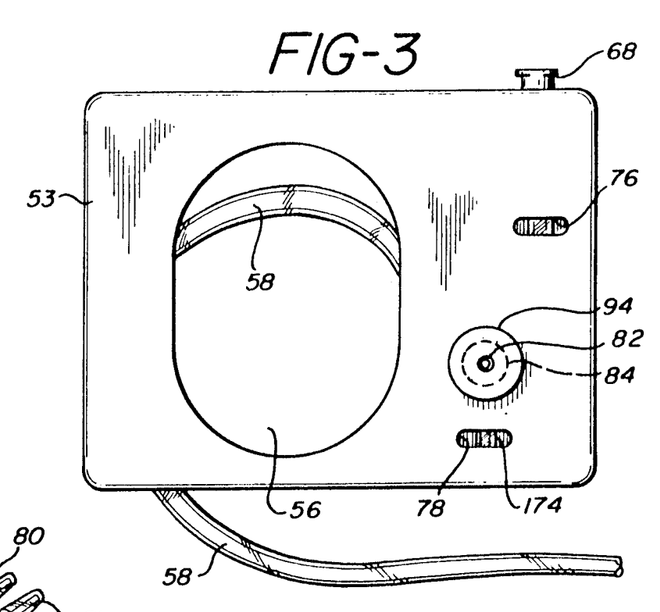
FIG. 3 is a rear plan view of the cassette of FIG. 2.
Figure 4:
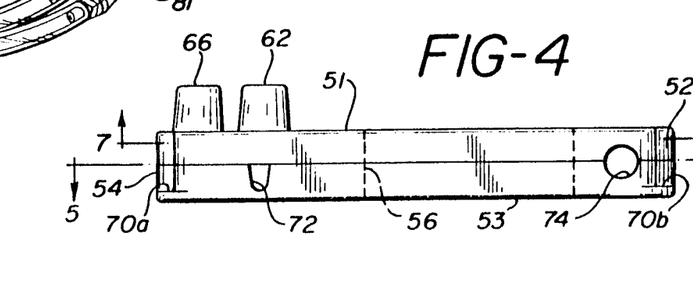
FIG. 4 is a bottom plan view of the cassette of FIG. 1.

Referring to FIGS. 2-4, views of the outside of a cassette 50 suitable for use with the module 10 are shown. FIG. 2 illustrates the front surface 51 of the cassette. The cassette is characterized by an oval opening 56 which accommodates the pump head. The width and arc of the opening 56 are sized to be just slightly larger than the pump head.

Located at the top of the cassette is an inlet luer 68 of the infusion line. The infusion line exits the cassette through tubing 64. The tubing 64 is connected to a barbed fitting within the cassette. This connection is protected by a molded guard 66 which projects from the front 51 of the cassette. The guard 66 is also shown in FIG. 4. The infusion tubing 64 terminates in a luer 81, by which the tubing may be connected to the infusion port of an infusion/aspiration handpiece or a surgical cutting instrument.

A suction tubing line 60 has a molded adapter piece 80 connected at its free end for connection to the suction, or aspiration, port of the handpiece or instrument. Tubing 60 is similarly connected to a barbed fitting within the cassette which is protected by a molded guard 62. The suction line passes through the cassette and makes a transition to a pump tubing segment 58. The tubing segment 58 enters the opening 56 through an aperture in the interior wall of the opening, passes along the inside wall along its upper arc, and exits the opening through an aperture in the interior wall on the opposite end of the arc from which it entered. The tubing segment is made of a material suitable for use in a peristaltic pump, such as silicone.

The tubing segment 58 exits the cassette through a hole in the bottom, from which it leads to a means for disposing of aspirated material such as a drain bag.

Along each vertical side of the cassette 50, the body of the cassette is thinned to form corner tabs 70a and 70b. These corner tabs fit snugly into the retaining brackets 20a and 20b of the module 10.

FIG. 3 shows the back surface 53 of the cassette 50, including the previously described infusion line inlet luer 68, the opening 56, and pump tubing segment 58. Also shown are an aperture 76 through which the interrupter bar of opening 26 enters the cassette, and an aperture 78 for assage of the interrupter bar of opening 28. A vent line tubing segment is visible through aperture 78, and an infusion tubing segment is visible through aperture 76. There is a hole 94 through the back of the cassette for passage of a pressure sensing port 82, which mates with the port 22 when the cassette is mounted on the module 10. The port 82 is surrounded by a foam sealing gasket 84.

FIG. 4 is a bottom view of the cassette 50, which is seen to be comprised of a front half 52 and a back half 54. Guards 66 and 62 which extend from the front surface 51 are shown at the top of the drawing. Aperture 74 is provided for passage of tubing segment 58, which for clarity is not represented in FIG. 4. Aperture 72 is an opening for the vent line. On either side of the cassette bottom the corner tabs 70a and 70b may be seen.

Figure 5:
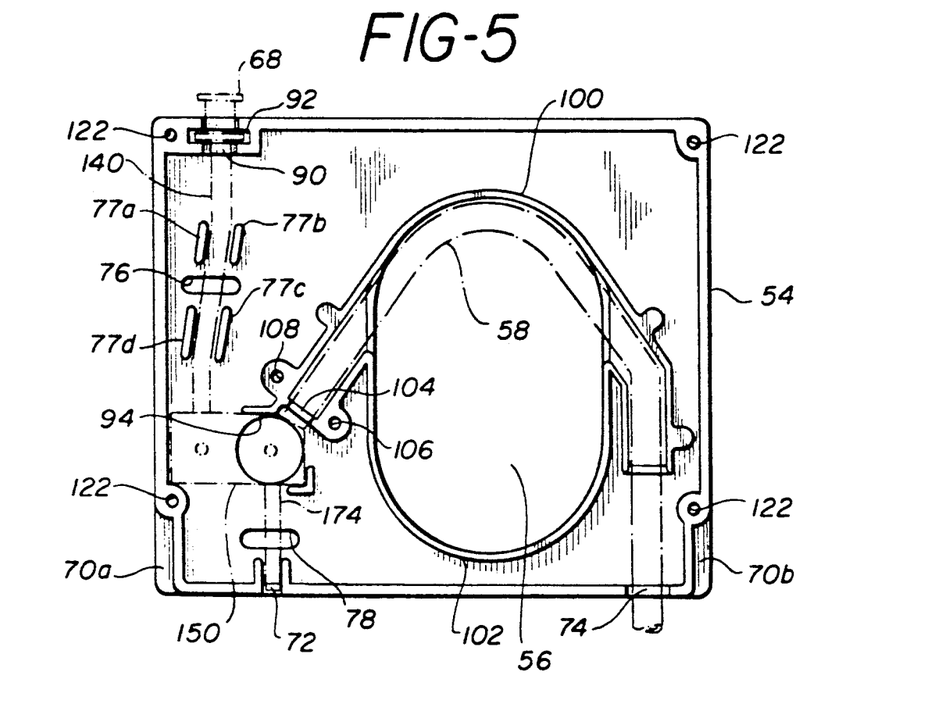
FIG. 5 is an internal view of the back half of the cassette of FIG. 2 taken along line 5—5 in FIG. 4.

Referring to FIG. 5, the interior of the back cassette half 54 is shown, with tubing segments and a junction block 150 drawn in phantom for ease of illustration. The infusion luer 68 enters the top of the cassette through a semicircular aperture in a block 90. The block 90 includes a rectangular opening 92 which retains a collar of the luer 68 to hold the luer in place. An infusion line tubing segment 140 extends from the luer 68 to the junction block 150. The tubing segment 140 passes over the interrupter bar aperture 76, and is maintained in this position by four molded guides 77a-77d. Vent tubing segment 174 extends from the junction block 150 to the aperture 72 and passes over the interrupter bar aperture 78.

The pump tubing segment 58 is retained in its intended position by a molded upper guide 100 and the opposite ends of a molded lower guide 102. A curved, molded protrusion 104 spans the two guides proximate the junction block 150 to serve as a portion of an integral clamp which secures the tubing segment 58 on its junction block fitting. A molded bracket with holes 106 and 108 at the ends of the location of protrusion 104 mates with pins in the front cassette half to secure the integral tubing clamp.

A portion of the upper guide 100 is seen to be contiguous with the upper arc of the opening 56. This portion of the guide serves two further purposes: it forms the upper interior wall of the opening 56, and it is the surface against which the tubing segment 58 is compressed by the pump head. The central portion of the lower guide 102 similarly is contiguous with the perimeter of the opening 56, and likewise forms the side and lower arcuate interior walls of the opening. It may be seen that the spaces between the two guides at their intersections with the opening perimeter form the apertures through which the pump tubing segment 58 enters and exits the opening 56.

Located at the upper two corners of the back cassette half 54 and just above each of the tabs 70a and 70b are holes 122 which mate with pins of the front cassette half 52.

Figure 7:
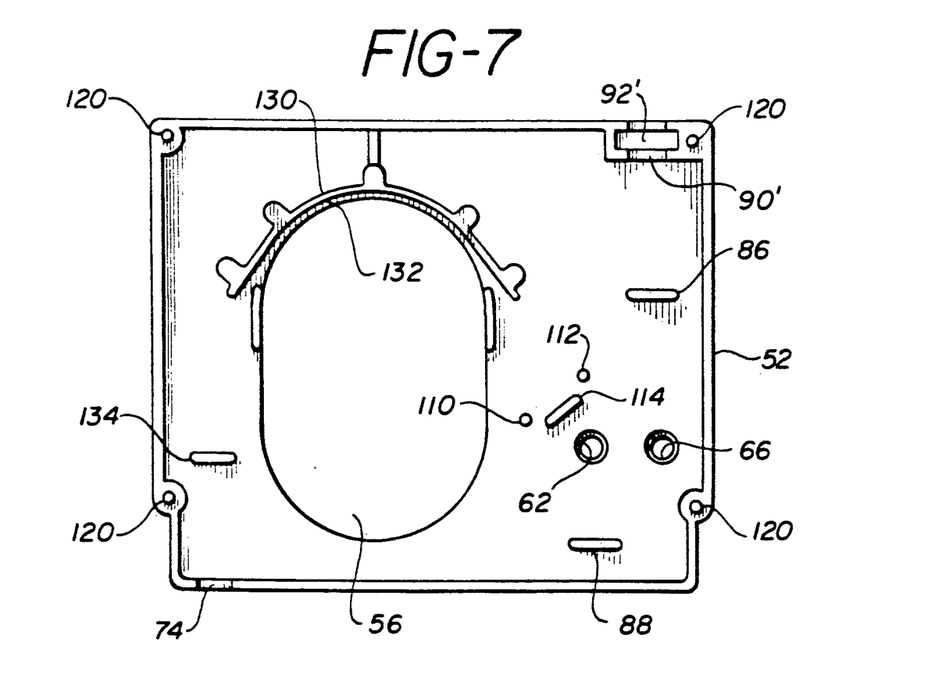
FIG. 7 is an internal view of the front half of the cassette of FIG. 2 taken along line 7—7 in FIG. 4.

FIG. 7 shows the interior of the front cassette half 52. A block 90' with an opening 92' mates with block 90 of the back cassette half to capture the luer 68 and its collar. A protrusion 86 forms an anvil surface for occluding tubing segment 140. The interrupter bar entering the cassette through aperture 76 will squeeze and thereby occlude the infusion line tubing segment 140 between the interrupter bar and the protrusion 86. Below the protrusion 86 are two holes through which the molded guards 62 and 66 on the front surface of the cassette may be seen. Below the hole surrounded by guard 62 for the suction line is a protrusion forming an anvil surface 88. The interrupter bar entering aperture 78 occludes the vent tubing segment 174 between the protrusion 88 and the interrupter bar.

Curved protrusion 114 extends to form the second half of the integral clamp which secures tubing segment 58 on its junction block fitting when the two cassette halves are mated together. Pins 110 and 112 fit into holes 106 and 108 of the molded bracket in the back cassette half to secure the integral clamp for the pump tubing segment. A protrusion 134 fits between the ends of the guides 100 and 102 where the tubing segment 58 leaves the two guides.

Located around the upper arc of the opening 56 is a reinforced support wall 130. The support wall 130 is spaced slightly above the perimeter of the opening so that the upper guide 100 of the back cassette half will fit flush against surface 132 of the support wall. The support wall thus supports the upper arcuate portion of the guide 100 where it opposes the compressive forces of the pump head rollers as the tubing segment 58 is compressed.

Located at the upper corners of the front cassette half and just above the tab locations are pins 120, which mate with the holes 122 in the back cassette half. It may be seen that when the two cassette halves are mated together, they are fastened to each other by the four pins 120, pins 110 and 112, and their respective holes.

Figure 6:
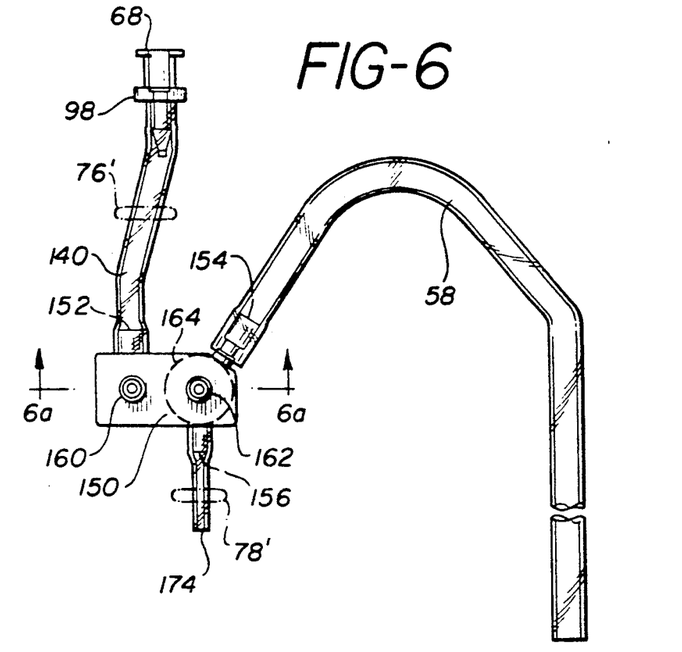
FIG. 6 is a view of the junction block and associated tubing segments shown in FIG. 5.

FIG. 6 illustrates the cassette tubing segments and junction block which were shown in phantom in FIG. 5, and in the same configuration. FIG. 6 clearly shows the collar 98 of the infusion line female luer 68 which fits into the rectangular openings 92, 92' of the cassette halves. The phantom lines 76' indicate the location of aperture 76 behind the infusion line tubing segment 140 in an assembled cassette. The infusion line tubing segment 140 is connected to a luer 152 on the junction block 150, and the vent tubing segment 174 is connected to a luer 156 on the junction block. The location of aperture 78 relative to the vent tubing segment in an assembled cassette is indicated by phantom lines 78'.

The pump tubing segment 58 is connected to a fitting 154 on the junction block. The fitting 154 has a narrow diameter neck, about which the integral clamp of the cassette secures the tubing segment to the fitting 154. Barbed fittings 160 and 162 extend normal to the plane of the drawing for connection to infusion tubing 64 and suction tubing 60. The fittings 160 and 162 are more clearly shown in FIG. 6a, which is a cross-sectional view of the junction block 150.

Figures 6A, 8:
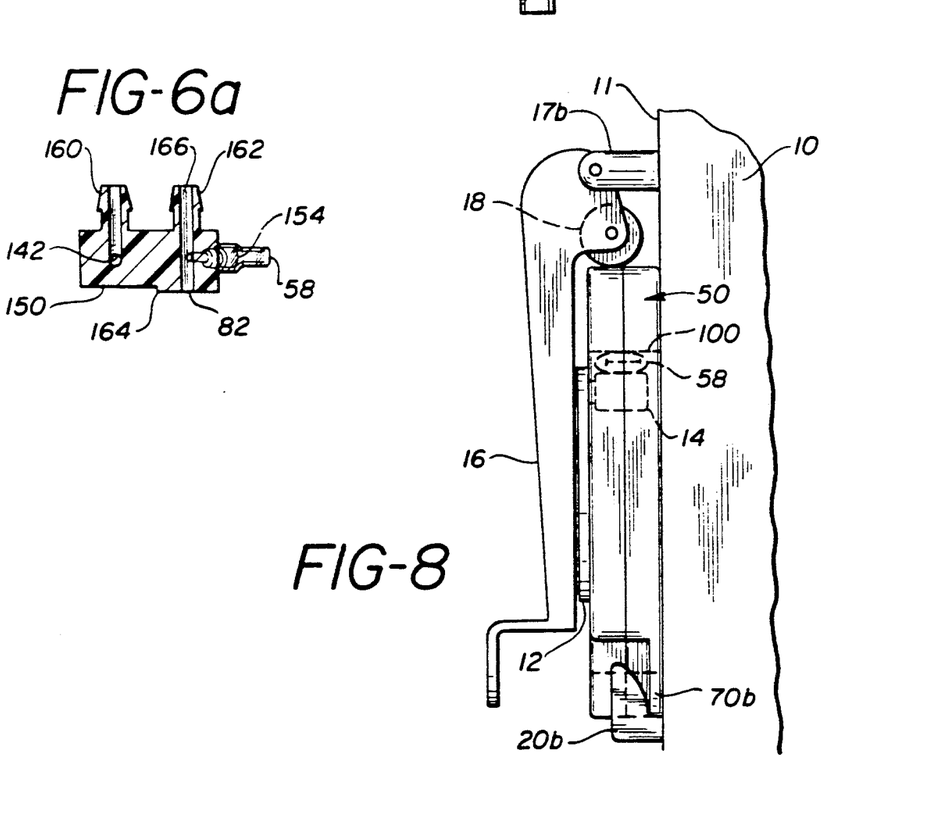
FIG. 6a is a cross-sectional view taken along line 6a—6a of FIG. 6.
FIG. 8 is a side view of the cassette of FIGS. 2-7 when mounted on the module of FIG. 1.

In FIG. 6a, the fluid passageways through the junction block 150 can be seen. A passageway 142 for the infusion line enters the junction block through fitting 152 on the back of the block as it is oriented in FIG. 6a, and continues through the barbed fitting 160. A suction line passageway 166 passes through the barbed fitting 162 and continues through the fitting 154. The extension of passageway 166 to the bottom of the junction block in FIG. 6a forms the pressure sensing port 82. The pressure sensing port 82 is surrounded by a raised mounting surface 164 for the sealing gasket 84 of FIG. 3. The diameter of surface 164, shown in phantom in FIG. 6, is sized to just fit into the hole 94 in the back half of the cassette (FIGS. 3 and 5).

FIG. 8 illustrates a side view of the cassette 50 when mounted for operation on the module 10. The mounted cassette is supported at the bottom by the placement of the corner tabs 70a and 70b in the retaining brackets 20a and 20b. This placement locates the cassette in its correct horizontal position on the module so that the cassette can be positioned with its back surface 53 flush against the front panel 11 of the module. In this position the pump head 12 extends through opening 56. The cassette is slightly raised from its final vertical alignment, as the tubing segment 58 is resting uncompressed between the pump head 12 and the guide wall 100.

To lower the cassette to its intended vertical alignment with the module, the latch 16 is pivoted downward over the cassette. This causes the cam bar 18 to first contact the upper front edge of the cassette, then to forcibly roll on to the top of the cassette, as shown in FIG. 8. The cam bar 18 thus presses the cassette downward with the corner tabs 70a and 70b firmly seated in the retaining brackets, and at the same time compresses tubing segment 58 between the guide wall 100 and the rollers 14 of the pump head 12. The interrupter bar apertures 26 and 28 of the module are then aligned with their corresponding apertures 76 and 78 on the back of the cassette. The pressure sensing ports 22 and 82 are likewise aligned.

Figure 9:
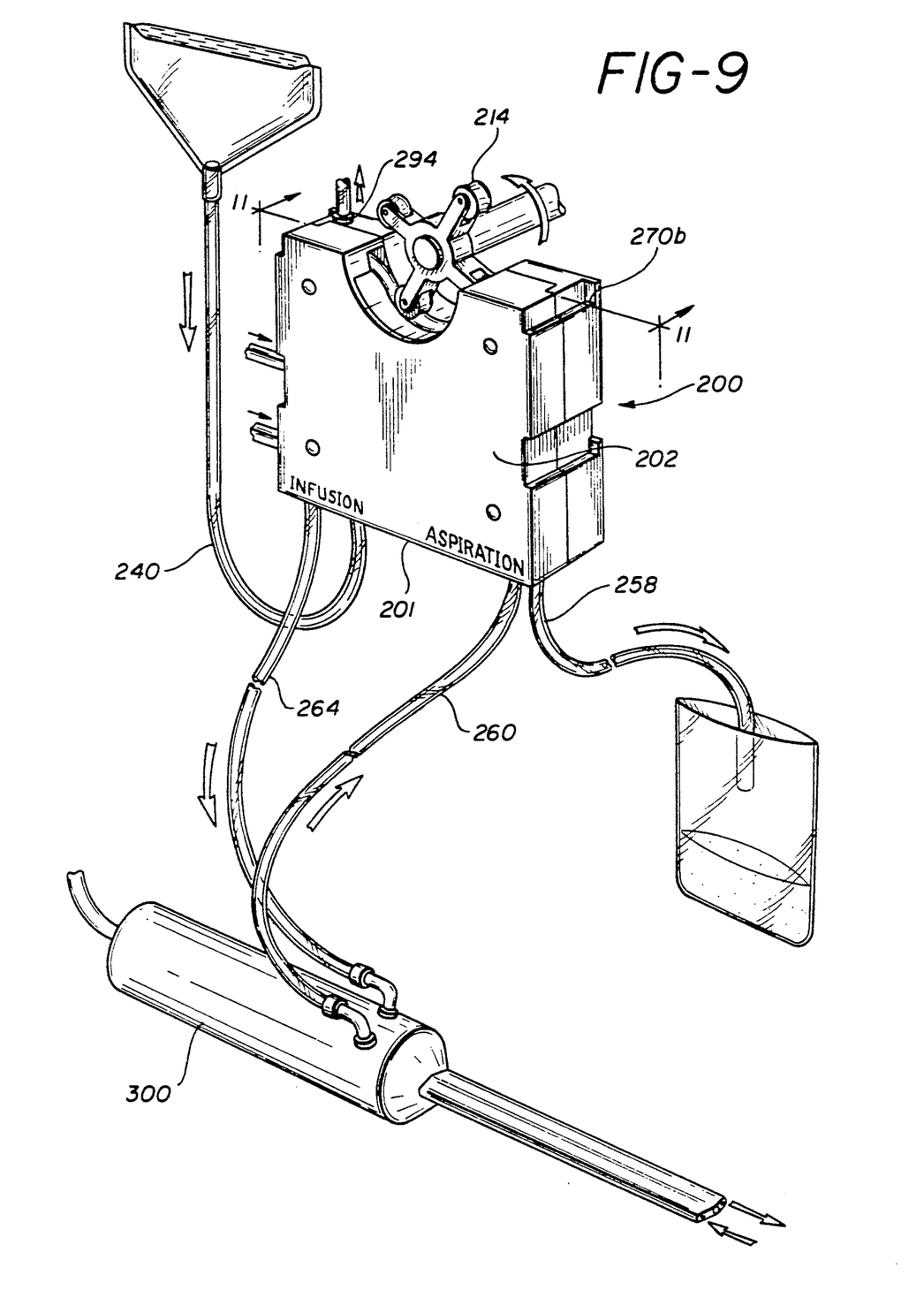
FIG. 9 is a front view in perspective of a second preferred embodiment of the cassette of the present invention interacting a peristaltic pump module.
Figure 10:
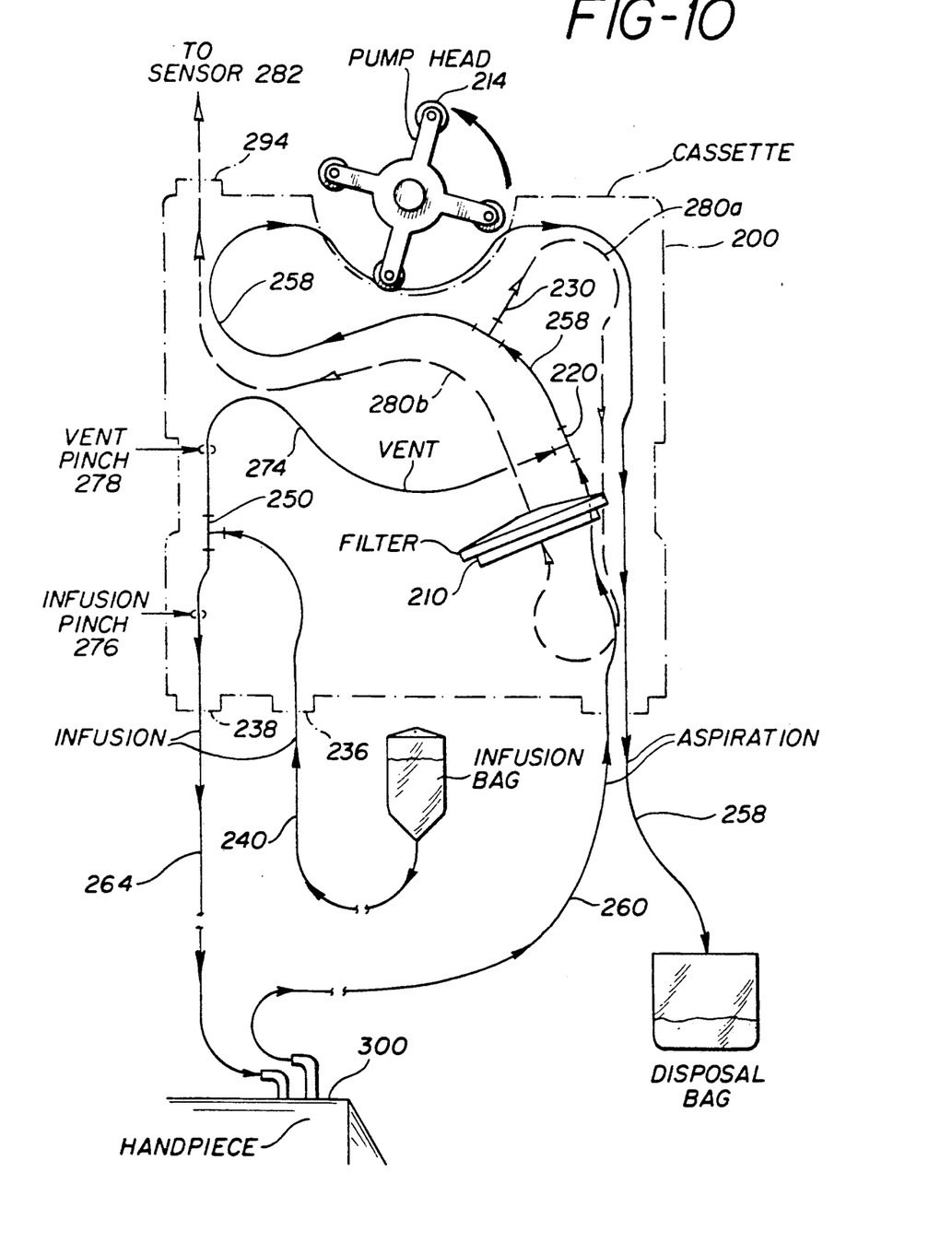
FIG. 10 is a schematic view of the cassette of a second preferred embodiment of the present invention when using a peristaltic pump module.
Figure 11:
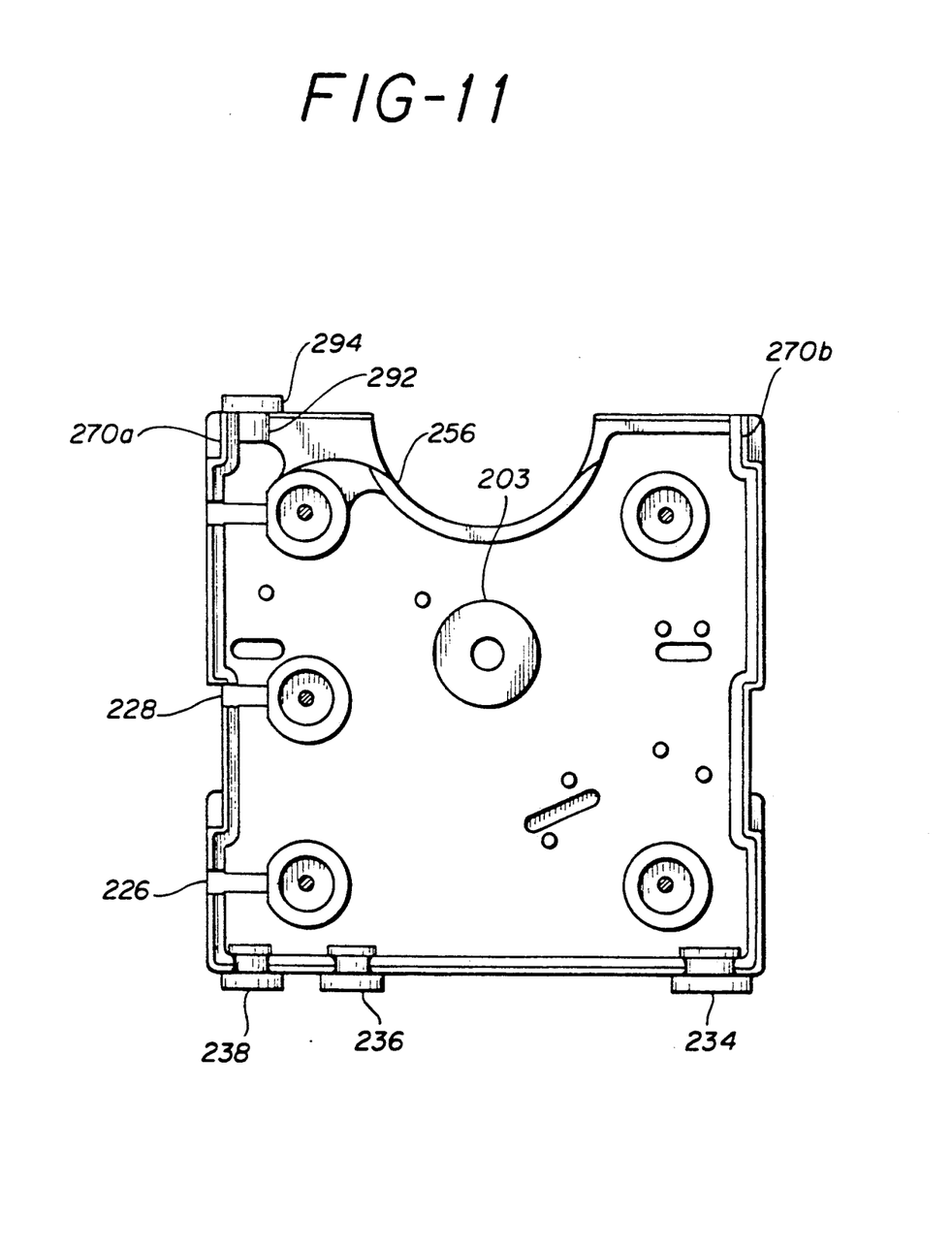
FIG. 11 is an internal view of the back half of the cassette of FIG. 9 taken along line 11—11 of FIG. 9.

Alternately, the cassettes 200, 300, 400, 500, as seen in FIGS. 9 through 14 can be used as a second preferred embodiment of the cassette of the present invention. The advantage of these types of cassettes is that they may be used with both a peristaltic pump system as well as a vacuum pump aspiration system. For example, as seen in FIGS. 9, 10 and 11, the cassette 200 is used with a peristaltic pump. There are tabs 270a and 270b which allow the cassette to be emplaced within the console 10 as seen in FIG. 1. Alternatively, cassette 200 may be emplaced within console 900 as seen in FIG. 15, by inserting tabs 270a, 270b into grips 910. The pump head 920 then is secured to cassette opening 256. Perpendicular forces are applied to sides 201, 202 of the cassette 200 in order to engage and align the cassette 200 with pump head 920 within grips 910. If latch 930 on console 900 is not securely engaged with cassette port 203 as seen in FIG. 11, a switch within console 900 will disable pump head 920. Returning to FIG. 1, the grips 17a, 17b and the roller head 214 are modified so that the rollers act along the edge of the cassette. The roller heads 214 fit securely within opening 256 of the cassette. Between opening 256 and the roller heads 214 is placed pump tubing segment 258, to affect peristaltic pumping. Pump tubing segment 258 leads out of cassette 200 in order to engage roller heads 214, then returns into the cassette 200 finally exiting at aperture 234 in order to lead to the disposal bag as seen in FIG. 9.

In addition, the infusion lead 240 enters the cassette 200 at aperture 236 and will engage infusion pinch 276. From the infusion pinch 276 the infusion exit tube 264 leads out of cassette 200 at aperture 238. Before engaging the infusion pinch 276, which enters the cassette 200 at aperture 226, the infusion lead 240 enters at T-shaped intersection 250 which contains the vent segment 274. The vent segment 274 passes between the vent pinch 278, which enters the cassette 200 at aperture 228. The vent segment 274 engages the aspiration input lead 260 and the pump segment 258 at T-shaped intersection 220.

Turning now to the aspiration input lead 260, it exits the handpiece 300 and is guided past the T-shaped intersection 230 where it becomes pump segment 258. Pump segment 258 also engages T-shaped intersection 230 which leads to sensing 280a. Pump segment 258 continues through the cassette 200 in order to engage peristaltic pump roller heads 214. Pump segment 258 then exits the cassette at aperture 234.

Finally, sensing segment 280a leads into filter 210 and through port 292 and seal 294 into sensor 282. Sensor 282 is able to determine the pumping pressure that the roller heads 214 are exerting on the pump segment 258. Roller heads 214 can therefore be adjusted to obtain the correct amount of pumping. In addition, vent segment 274 is able to vent pure fluid from the infusion line 240 to the aspiration line 260.

It will be noticed that the cassette 200 as constructed in the embodiment shown in FIGS. 9, 10 and 11, has two distinct advantages. First, the interaction between any irrigation/aspiration module and the cassette 200 takes place in the same plane. This creates less stress on the cassette and the irrigation or aspiration lines, and decreases the possibility of excess forces and moments. In addition, it makes latching and unlatching the cassette easier. Also, it will be noticed that because the roller heads 214 engage only a small arc of the pump segment 258, lesser forces are exerted on the pump segment 258. This ease of emplacement and reduction of forces makes the use of this second embodiment of the cassette 200 highly desirable.

Figure 12:
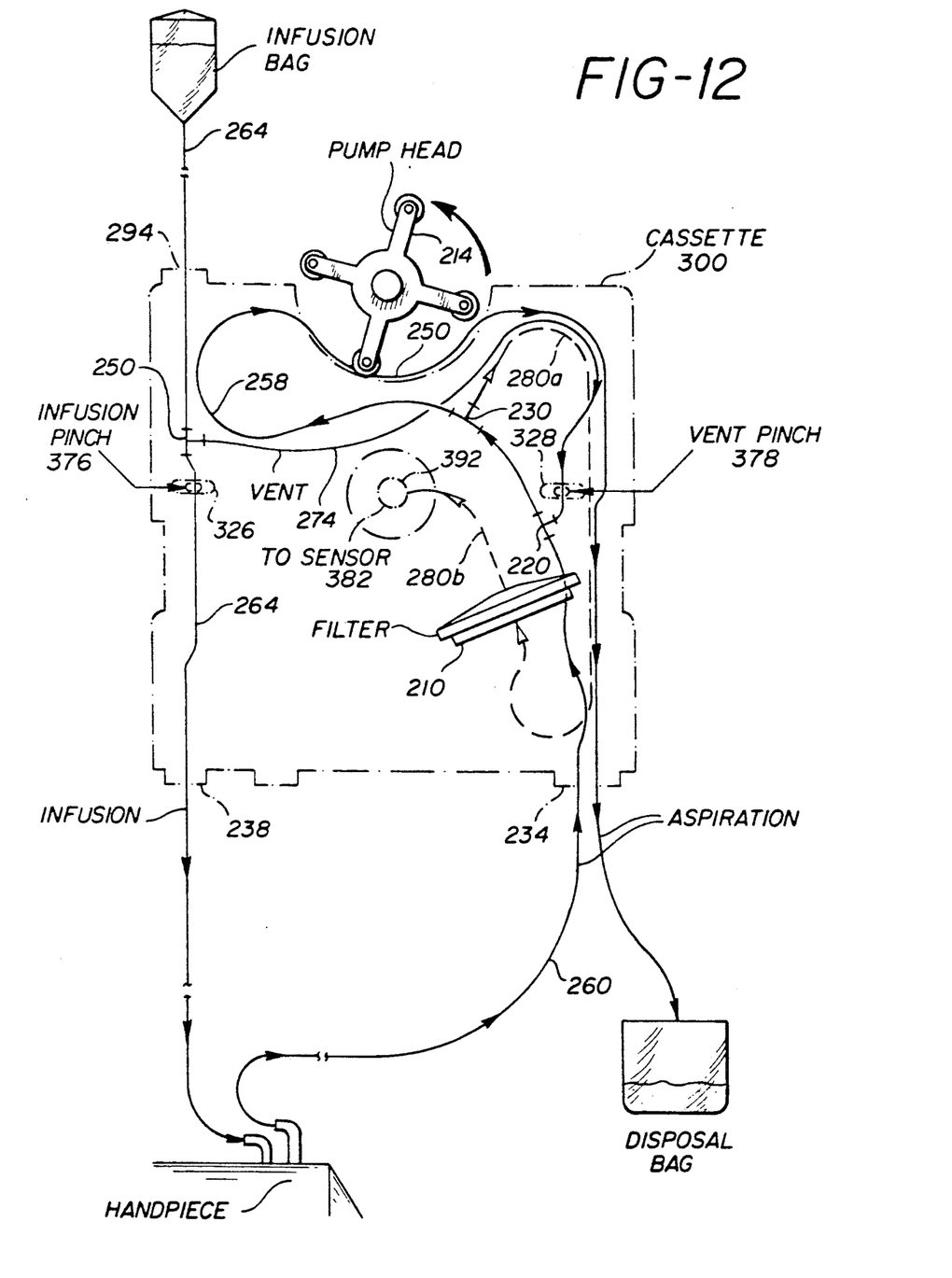
FIG. 12 is a schematic view of an alternate use of a peristaltic pump with the cassette of the present invention.

The cassette of the present invention can be modified so that the occludable openings of the console 10 or console 900 can be used. As seen in FIG. 12, infusion pinch 376 enters the cassette 300 through aperture 326, which lies on the bottom of the cassette 300. Also, vent pinch 378 lies underneath the cassette 300 and enters through aperture 328. Similarly, sensor 382 lies underneath cassette 300 and line 280b exits the cassette at port 392. A plunger 394 as seen in FIG. 15 is inserted into port 392. The plunger 394 serves to seal sensing line 280b leading to sensor 382. Plunger 394 when inserted into port 392 also serves to latch cassette 300 to console 900. Thus, in this embodiment, the planes of the tubing lines will turn at 90° angles.

While the function of the cassette will operate identically, the benefits obtained by operating in a single plane are not apparent. That is, again, infusion line 264 engages T-shaped intersection 250 in order to lead to infusion exit 264. Also engaging T-shaped intersection 250 is vent segment 274, which leads to aspiration input 260 at T-shaped intersection 220. Aspiration input line 260 enters the cassette 300 at aperture 234 and leads into pump segment 258 which engages roller heads 214 at arc-shaped exterior 256 of the cassette 300. Again, sensing line 280a exits the aspiration line 260 at T-shaped intersection 230, and leads through filter 210 to sensor 382. Pumping is adjusted at the sensor 382.

Figure 13:
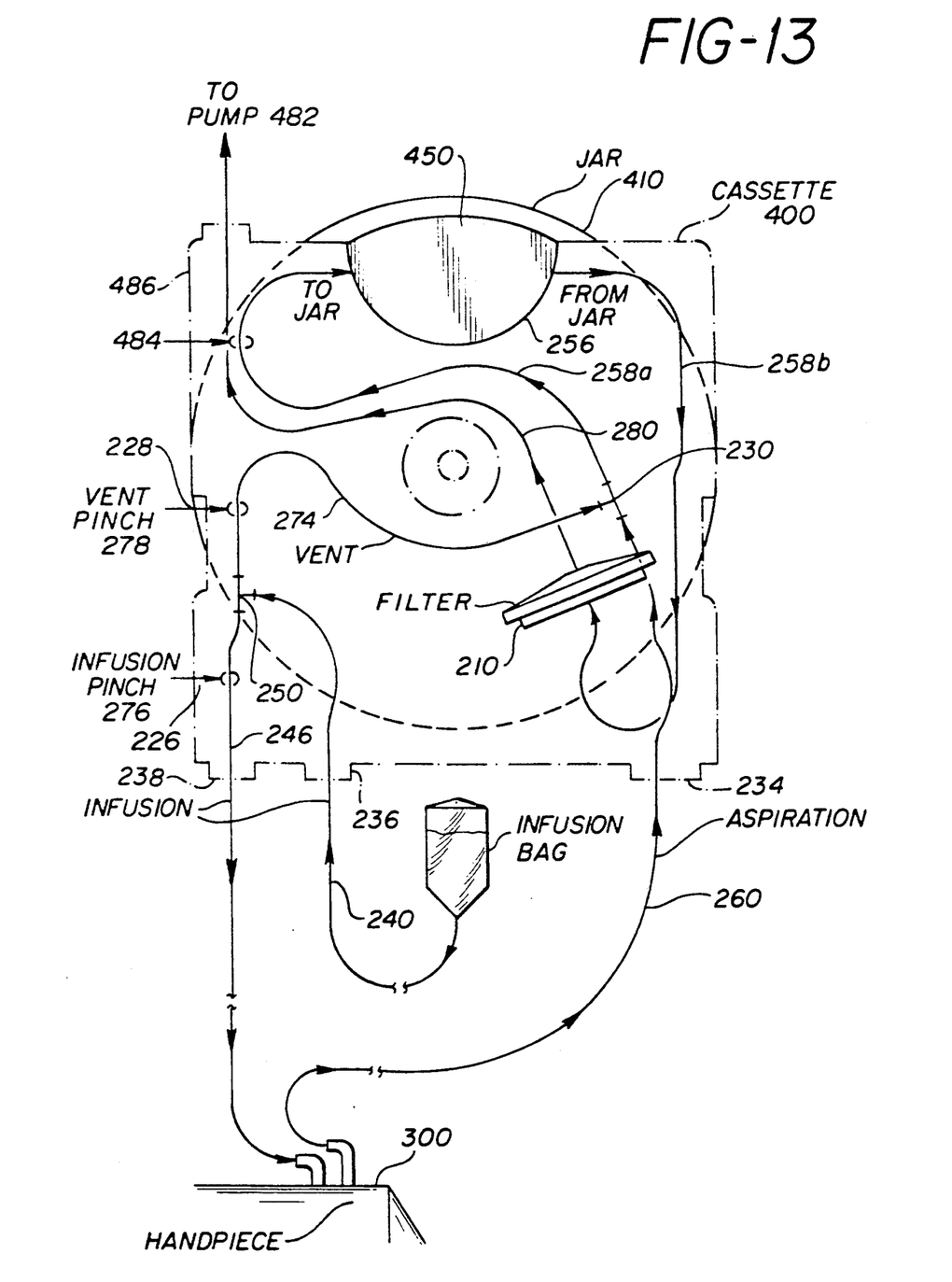
FIG. 13 is a schematic view of the cassette of the present invention when used with a conventional vacuum pump system.

It is possible to use the second preferred embodiment of the present cassette in a vacuum tubing system. As seen in FIG. 13, cassette 400 has been so modified.

Infusion line 240 enters cassette 400 at aperture 236. Infusion line 240 then engages T-shaped intersection 250 to lead to infusion exit line 246. Infusion exit line 246 then leads to hand piece 300. Infusion exit line 264 can be pinched at infusion pinch 276 which engages the cassette 400 at aperture 226. Also leading from T-shaped intersection 250 is vent segment 274, which encounters vent pinch 278 engaging the cassette 400 at aperture 228. Vent 274 leads from infusion line 240 to the aspiration input line 260, which it engages at T-shaped intersection 230. Aspiration input line 260 enters the cassette at aperture 234 and engages T-shaped intersection 230.

Of course, because peristaltic pumping is no being used, there must be an adaptation made in the cassette 400 to engage the vacuum pump of the present system. This is evident is semicircular fitting 450. This semicircular fitting 450 fits within the arc-shaped section 256 of the cassette 400 in order to engage the cassette 400 and the aspiration line. Semicircular fitting 450 is an adapted part of refuse jar 410 as commonly disclosed in all vacuum pump type systems. Therefore, refuse jar 410 will receive the refuse from aspiration line 258a so that aspiration line 258b will be clear of refuse. Again, aspiration line 258b will lead into filter 210 so that suction sensing line 280 will be clear of refuse.

Suction sensing line 280 will lead to a sensor not shown, in order to regulate pump 482. There is a sensor pinch at 484 which enters the cassette 400 at aperture 486. This aperture 486 is able to close the suction sensing line 280 and pump line 258b in order to stop pumping within the aspiration line 258b. It is to be noticed that again, pumping, infusion and aspiration take place in the same plane along the cassette 400.

Figure 14:
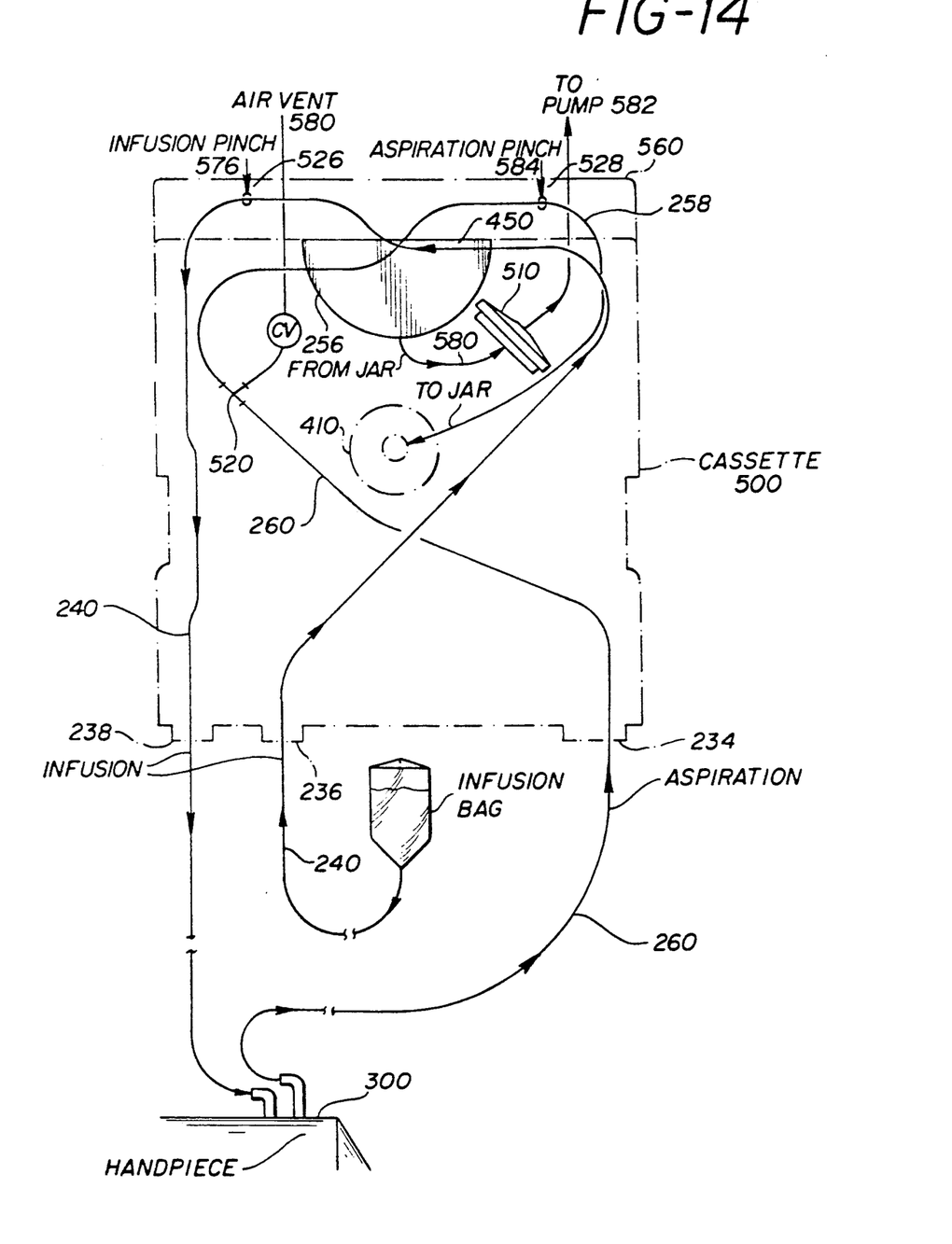
FIG. 14 is a schematic of an alternate use of the cassette of the present invention with a conventional vacuum pump system.
Figure 15:
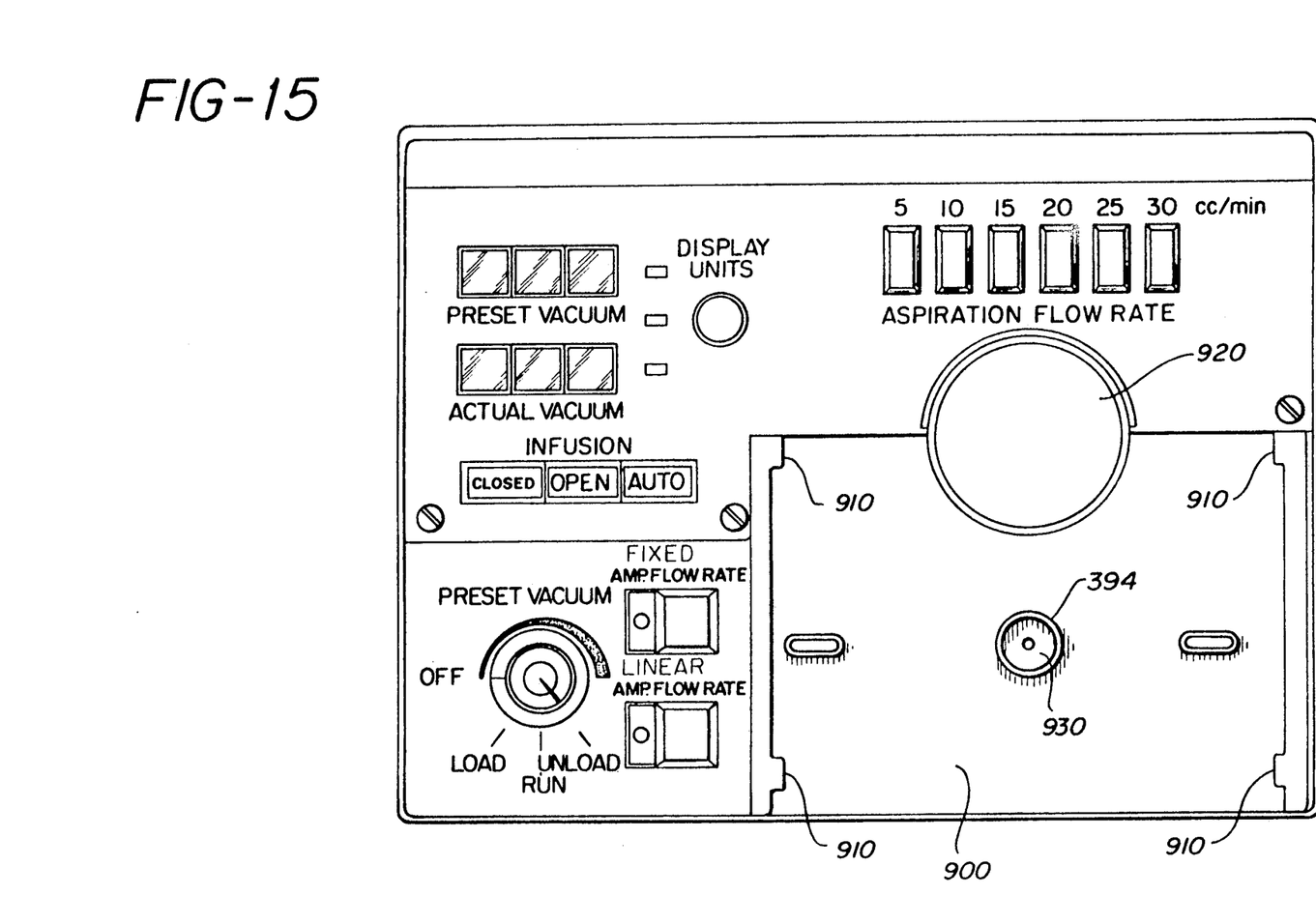
FIG. 15 is a front plan view of a console for use in conjunction with a second embodiment of the cassette of the present invention as seen in FIG. 12.

Finally, if it is desired to use the cassette of the present invention with a air vent s disclosed in previous systems, this embodiment is possible as seen in FIG. 14. There, cassette 500 contains infusion line 240 which enters the cassette at aperture 236. The infusion line 240 leads into fitting 560, which has been attached to cassette 500. On this attachment 560, the infusion line 240 encounters infusion pinch 576 which enters the attachment 560 at aperture 526. Infusion 240 then exits the cassette 500 at aperture 234, and leads to hand piece 300. Aspiration line 260 also enters the cassette at aperture 234 and will flow into T-shaped intersection 520. The aspiration line 260 can be then vented to air through air vent 580. The aspiration line 260 leads from T-shaped intersection 520 to aspiration exit line 258. This line 258 continues through arc-shaped exterior wall 256, then through semicircular fitting 450 and into fitting 560. Aspiration pinch 584 enters fitting 560 at aperture 528. The aspiration line 258 therefore returns into the cassette 500 and leads into jar 10 through the bottom of the cassette 500. Pumping line 580 leads from jar 410 through filter 510 and to pump 582.

The pump cassette systems in any of the embodiments are now ready for operation. As best seen in the system described in FIG. 1, the user sets the preset vacuum level with the knob 32 and its units of display with the knob 36. The suction rate is set by pressing one of pushbuttons 30, and the mode of suction control is set by setting one of switches 44 and 46. In the system where vacuum pumping is Possible, a modification is made to the console to include vacuum pumping. The infusion line may be controlled automatically by depressing pushbutton 42c, or pushbutton 42a may be pressed to close the infusion line until it is needed.

The fluid line is connected by connecting a source of infusion liquid to the female luer 68. Generally, this will be a bag or bottle of liquid suspended above the module, as seen in FIG. 9. Luer 81 and adapter 80 of tubing lines 64 and 60 are connected to the infusion and suction ports of the handpiece or surgical instrument, and the system may then be primed with liquid.

In operation with automatic infusion line control, where the control pedal is depressed the infusion line interrupter bar retracts to open the infusion line tubing segment. This occlusion control technique is the same as that used by the interrupter bars described in U.S. Pat. No. 4,493,695. Infusion liquid then flows through tubing segment 140, the junction block passageway 142, the barbed luer 160, and into the infusion tubing 64. Infusion is effected in the same fashion in subsequent embodiments.

Further depression of the control pedal causes the pump head to begin rotating, either immediately at its selected rate when fixed suction is set, or at a controlled accelerating rate to the selected rate if linear suction is called for. Suction then begins to build in the suction line 60, and is continuously monitored at the port 82 of the junction block by the module's internal pressure sensor. All the peristaltic pumps operate in the same fashion.

The pump head continues to rotate so long as the pump is freely pumping liquid. When the actual vacuum level reaches the preset vacuum level, as would occur if the suction port of the instrument or handpiece becomes fully occluded with particles of tissue, the pump head rotation stops until the actual vacuum level falls to a predetermined level, such as 80% of the preset maximum level. At this point the pump head resumes its rotation to aspirate the tissue particles through the suction line and away from the surgical site. Thus, there is no buildup of substantial suction pressure at the handpiece or instrument tip until an occlusion of the suction line occurs. This prevents the application of undesired suction pressures to the patient at the surgical site, and eliminates any tendency of the hand-held instrument to "grab" tissue, as would happen if continual suction were applied. The physician thus is more easily able to precisely control the instrument during the surgical procedure.

On the other hand, if vacuum pumping is desired, cassette 200 may be used as modified and seen in FIGS. 13 and 14 with cassettes 400, 500. While the infusion line operates identically as in the peristaltic system, the aspiration line will operate in the same way disclosed in U.S. Pat. No. 4,493,695. Of course, other than as disclosed with cassette 500, all the present embodiments are vented in fluid communication between the infusion and aspiration line.

When the depressed control pedal is released by the physician, the infusion segment 140 is occluded and the interrupter bar extending through aperture 78 of the cassette is momentarily retracted, opening the vent segment 174 and equalizing the suction line vacuum to atmospheric pressure. The handpiece or instrument can then be moved about the surgical site without exposing the patient to any residual vacuum pressures in the suction line.

What is claimed is:

1. A microsurgical irrigation/aspiration system, comprising:

an irrigation/aspiration instrument having pumping means with a plane along which pumping may take place; and removable cassette means containing an aspiration pumping segment which cooperates with said pumping means in the performance of either peristaltic or vacuum pumping, said cassette means having a wall defining an aperture for engaging said pumping segment with said pumping means, said cassette means being adapted for mounting to said instrument in the plane of said pumping means, said cassette means further including a selectably occludable infusion line passing therethrough.

2. The microsurgical irrigation/aspiration system of claim 1 further comprising mounting means securely engaging said pumping means with said aperture of said cassette.

3. The system of claim 1 wherein said instrument contains an outermost panel and said pumping means comprises roller head means for performing peristaltic pumping, axially extending from said outermost panel and including a plurality of rollers located in a plane offset from and parallel to the plane of said outermost panel and said removable cassettes means cooperating with said roller head means in the performance of peristaltic pumping, said cassette means engaging said roller head means so that said cassette is located in said offset plane and said aperture radially surrounds said rollers of said roller head means with said pumping segment located between said roller head means and said aperture.

4. The system of claim 3 wherein said aperture is larger than said roller head means to allow said cassette means to initially engage said roller head means without compressing said pumping segment.

5. The system of claim 4, further comprising mounting means extending from said outermost panel for securely engaging said roller head means in said aperture with said pumping segment compressed between said roller head means and said aperture.

6. A microsurgical irrigation/aspiration system comprising:
   a console including pumping means for performing either peristaltic or vacuum pumping, mounting means for engaging a pumping segment, and latch means for applying a compressive force to a disposable cassette; and
   a disposable cassette, having a pumping segment and having a wall including an opening for engaging and surrounding said pumping means by means of said pumping segment, and engaging means located on said cassette for engaging said mounting means;
   wherein said latch means applies a compressive force to said cassette to maintain the engagement of said engaging means and said mounting means and to maintain engagement of said pumping means with said pumping segment.

7. The system of claim 6 wherein said console includes roller head means for performing peristaltic pumping;
   said opening engages and surrounds said roller head means, said pumping segment located in said opening and opposing said wall of said cassette; and
   said latch means compresses said pumping segment between said wall and said roller head means.

8. A microsurgical irrigation/aspiration system, including:
   a disposable cassette having:
   an exterior wall abutting at least two other outer walls, each of said walls intersecting at a corner;
   an opening defined by a portion of said exterior wall for engaging and surrounding a pumping means, said pumping means capable of performing either peristaltic or vacuum pumping;
   a pumping segment for aspiration located in said opening and suitable for engagement with said pumping means for the performance of said pumping;
   mounting means located on said cassette for engaging bracket means on a console containing pumping means in order to mount said cassette on said console; and an irrigation segment extending through said cassette.

9. The system of claim 8 wherein said disposable cassette further includes means for allowing selective occlusion of said irrigation segment.

10. The system of claim 9 wherein said disposable cassette further includes a vent segment in liquid communication with said pumping segment.

11. The system of claim 10 wherein said disposable cassette further includes means for allowing selective occlusion of said vent segment.

12. The system of claim 11 wherein said disposable cassette further includes a suction measuring port in fluid communication with said pumping segment.

13. The system of claim 12 wherein said opening in said exterior wall, said means for selective occlusion of said irrigation segment, said means for selective occlusion of said vent segment, and said suction measuring port lie within the same plane of said disposable cassette.

14. The system of claim 13 wherein said means for selective occlusion of said irrigation segment, said means for selective occlusion of said vent segment, and said suction measuring port are located on the same outer wall of said disposable cassette.

15. The system of claim 14 wherein said mounting means comprises first and second tabs located at opposite corners of one outer wall of said cassette.

16. A microsurgical irrigation/aspiration system comprising a disposable cassette having:
   an exterior wall;
   an opening defined by a portion of said exterior wall for engaging a pumping means, said pumping means capable of performing either peristaltic or vacuum pumping;
   a pumping segment located in said opening and suitable for engagement with said pumping means for the performance of said pumping;
   mounting means located on a side of said cassette for engaging bracket means for mounting said cassette on a pumping means console;
   an irrigation segment extending through said cassette;
   wherein said disposable cassette opening engages and surrounds said pumping means; and
   pumping means comprising a roller head for peristaltic pumping, said pumping segment opposite said opening in said exterior wall.

17. The system of claim 16, wherein said disposable cassette further includes means for allowing selective occlusion of said irrigation segment.

18. The system of claim 17, wherein said disposable cassette further includes a vent segment in fluid communication with said pumping segment.

19. The irrigation/aspiration system of claim 18, wherein said disposable cassette further includes means for allowing selective occlusion of said vent segment.

20. The system of claim 19, wherein said disposable cassette further includes a suction measuring port in fluid communication with said pumping segment.

21. The system of claim 20 including a sensor containing a plunger for engaging said suction measuring port in order to latch said cassette to said console.

22. The system of claim 20 wherein said opening in said exterior wall, said means for selective occlusion of said irrigation segment, said means for selective occlusion of said vent segment, and said suction measuring port lie within the same plane of said disposable cassette.

23. The system of claim 22 wherein said means for selective occlusion of said irrigation segment, said means for occlusion of said vent segment, and said suction measuring port are located on the same outer wall of said disposable cassette.

24. The system of claim 23, wherein said mounting means comprises first and second tabs located at opposite corners of one outer wall of said cassette.

25. A microsurgical irrigation/aspiration system comprising:
    a disposable cassette having a body with t2o apertures and having a height and a width and exhibiting a thickness defining four walls and exhibiting major dimensions of an outer surface located in a plane defined by the height and width of said cassette body, an opening in said body for engaging and surrounding a pumping means, said pumping means capable of performing either peristaltic or vacuum pumping, a pumping segment extending through at least a portion of said opening for engagement with said pumping means, an irrigation segment extending through said cassette with an occludable portion of said irrigation segment opposite a first aperture in said cassette body, and a suction measuring line in fluid communication with said pumping segment and passing through a second aperture in said cassette body.

26. A microsurgical irrigation/aspiration system comprising:
    a disposable cassette having a body with two apertures and having a height and a width and exhibiting a thickness defining four walls, and exhibiting major dimensions of an outer surface located in a plane defined by the height and width of said cassette body, an opening in said body for engaging a pumping means, said pumping means capable of performing either vacuum or peristaltic pumping, a pumping segment extending through at least a portion of said opening for engagement with said pumping means, an irrigation segment extending through said cassette with a portion of said irrigation segment opposite a first aperture in said cassette body, and a suction measuring line in fluid communication with said pumping segment and passing through a second aperture in said cassette body, and a third aperture and a vent segment in fluid communication with said pumping segment, said vent segment selectively occludable through said third aperture in said cassette body.

27. The system of claim 26 wherein said first, second and third apertures in said disposable cassette are located on the same wall of said cassette body.

28. The system of claim 25 wherein said body opening engages a roller head capable of performing peristaltic pumping, said pumping segment opposes a wall on said cassette containing said opening and is compressed by roller head when said roller head are engaged with said cassette; and roller head capable of performing peristaltic pumping.

29. The system of claim 28 wherein said disposable cassette further includes a third aperture in said outer surface and a vent segment in fluid communication with said pumping segment, said vent segment selectively occludable through said third aperture.

30. The system of claim 29 further including a console containing said roller heads and latch means, and said cassette containing a suction sensing port engageable with said latch means in order to latch said pumping means to said cassette.

31. The system of claim 29 wherein said first, second and third apertures in said disposable cassette are located on the same wall of said cassette body.

* * * * *